United States Patent [19]

Richers

[11] 4,452,091
[45] Jun. 5, 1984

[54] SOIL GAS PROBE

[75] Inventor: David M. Richers, Glenpool, Okla.

[73] Assignee: Cities Service Company, Tulsa, Okla.

[21] Appl. No.: 391,253

[22] Filed: Jun. 23, 1982

[51] Int. Cl.³ .............................................. G01N 1/24
[52] U.S. Cl. .............................. 73/864.52; 73/864.74
[58] Field of Search ......................... 73/864.52, 864.74

[56] References Cited

U.S. PATENT DOCUMENTS

| 2,141,261 | 12/1938 | Clark ................................ | 73/864.74 |
| 3,374,678 | 3/1968 | McGuckin ........................ | 73/864.74 |
| 3,383,923 | 5/1968 | Conche et al. ................... | 73/864.52 |
| 3,835,710 | 9/1974 | Pogorski .......................... | 73/864.74 |
| 4,335,622 | 6/1982 | Bartz ................................ | 73/864.74 |

Primary Examiner—S. Clement Swisher
Attorney, Agent, or Firm—Robert H. Sproule; George L. Rushton; John W. Carpenter

[57] ABSTRACT

A purgable soil gas probe for removing small quantities of gases from the earth's soil to determine the presence of hydrocarbon deposits nearby. A removable evacuated container is attached to the upper end of the probe to withdraw soil gas through the probe into the container. A device such as a stop cock regulates the flow of external gases into the probe. The probe is purged by attaching a first evacuated container to withdraw any contaminating gases within the probe, and then replacing it with a second evacuated container to withdraw the soil gases to be analyzed.

10 Claims, 6 Drawing Figures

SOIL GAS PROBE

BACKGROUND OF THE INVENTION

This invention relates to an apparatus for withdrawing small quantities of gases from the soil for later laboratory analysis. More particularly the invention relates to an apparatus which may be purged of all contaminating gases prior to withdrawing the soil gas sample thereby providing a more accurate analysis of the gases present in the soil.

The contents of a soil gas sample may indicate the presence of hydrocarbon deposits nearby. Due to the small quantity of gas collected from the soil, it is imperative however that any analysis include only those gases present in the soil itself. U.S. Pat. No. 4,261,203 discloses a soil probe having a movable tip for covering and uncovering inlet ports in the lower end of the probe. When the probe is inserted into the ground, the inlet ports are uncovered and soil gas is withdrawn into a vacuum type container. The movable tip prevents atmospheric gases from entering the probe after the vacuum container is attached; however, the probe lacks any closure means at the outlet end of the probe to allow pre-purging of contaminant gases prior to attachment of the vacuum container. U.S. Pat. No. 2,141,261 by Clark discloses a soil probe utilizing a removable vacuum container. The Clark patent also lacks a means for sealing the upper end of the probe from the outside atmosphere to allow purging of the probe. Therefore any soil gas collected in the vacuum container is contaminated by gas present in the probe when the soil gas sample is collected.

My invention, on the other hand, teaches that pre-purging of the probe prior to withdrawing a test sample is necessary to remove any gas remaining in the probe which would contaminate the test sample. Unlike my invention, pre-purging of the prior art apparatuses is impossible, however, because the prior art lack any means for sealing the upper end of the probe when the vacuum or evacuated container is removed from the probe.

SUMMARY OF THE INVENTION

The apparatus comprises a shaft including a capillary bore transversing the length of the shaft. The shaft has a first end and a second end, the second end having at least one conduit in communication with both the capillary bore and the soil so that soil gases may pass through the conduit. Means are positioned in proximity to the first end of the shaft for coupling a gas collecting container to the shaft to allow soil gases to be withdrawn from the soil through the capillary bore into the container. Another means, positioned between the coupling means and the second end of the shaft, regulates the flow of gases into and out of the capillary bore through the first end of the shaft.

Sample gases are collected from the earth's soil by inserting a soil gas probe into the earth's soil, attaching to the apparatus a first gas collecting container for purging the apparatus, opening a regulating means to allow contaminant gases to be withdrawn from the apparatus into the first collecting container while simultaneously allowing gases from the soil to be withdrawn into the apparatus, closing the regulating means, replacing the first collecting container with a second gas collecting container for obtaining a test sample, and opening the regulating means to allow the soil gas to be withdrawn from the probe into the second collecting container.

It is therefore an object of the present invention to provide a soil gas probe for collecting soil gases.

It is another object of this invention to provide a soil gas probe having a device to regulate the flow of gases through the top of the probe.

It is yet another object of this invention to provide a process for purging the soil gas probe prior to collecting the sample so that a sample free of contaminant gases is obtained.

These, together with various ancillary objects and features which will become apparent as the following description proceeds, are obtained by the novel apparatus, preferred embodiments being shown in the accompanying drawings, by way of example only, wherein:

DETAILED DESCRIPTION OF THE INVENTION

Figure 1:
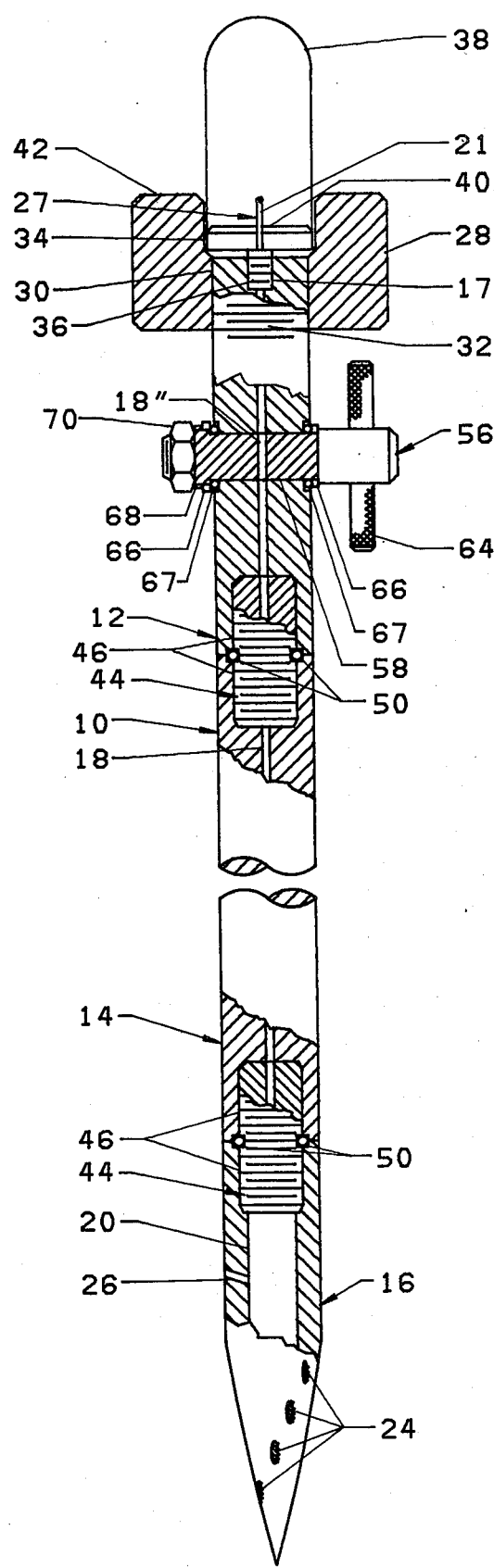
FIG. 1 is a partial sectional view of the probe with the stop cock in the open position.
Figure 2:
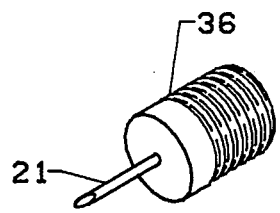
FIG. 2 is a perspective view illustrating the hollow tube and hollow tube threaded connector.

Referring in detail now to the drawings wherein like or similar parts of the invention are identified by like reference numerals, FIG. 1 defines a shaft, generally illustrated as 10, comprising three parts, an upper sleeve generally illustrated as 12, a body generally illustrated as 14, and a tip generally illustrated as 16. Upper sleeve 12, body 14 and tip 16 may be constructed of some durable material such as stainless steel. The total length of the three parts may be from about 5½ feet to about 6 feet with a diameter of about one inch at the widest part. Tip 16, tapers inwardly to terminate in a conical point. A capillary bore 18 about 0.032 inches in diameter longitudinally transverses the inside of shaft 10. Capillary bore 18 terminates at one end in a void space 20 located inside tip 16, void space 20 having a volume of about five cubic centimeters. Capillary bore 18 terminates at the other end in threaded female receptacle 17 formed in the top of shaft 10. A plurality of openings 24 are connected by conduits 26 to void space 20. Upper sleeve 12 includes a means, generally illustrated as 27, for coupling a gas collecting container 38 to shaft 10 such that bore 18 is in gas tight communication with container 38. Collecting container 38 may comprise an evacuated container such as a Vacutainer (a trademark of Becton-Dickinson Co.) or any other removable container which contains a vacuum or produces a suction to withdraw gases from the soil through bore 18 and into container 38. The typical volume of collecting container 38 is from about 20 to about 22 cubic centimeters. As depicted in FIG. 1, coupling means 27 includes block 28 with threaded opening 30 to mate with threads 32 located on the exterior surface of upper sleeve 12; block 28 also includes well 34 which concentrically aligns with opening 30. Hollow tube 21 (FIG. 2), made of 20 gauge stainless steel tubing or the like, is attached to shaft 10 by threaded male connector 36 which mates with threaded female receptacle 17 through the top of shaft 10. Threaded connector 36 is press fit to tube 21 to form a gas tight fitting with bore 18 when screwed into receptacle 17. Collecting container 38 is sized to fit within well 34 such that the sharpened end of tube 21 punctures septum 40. Septum 40 is made of expandable rubber or other similar material which contracts to form a gas tight seal around tube 21 when tube 21 is inserted therein. Block 28 includes a striking surface 42 for receiving a driving force from a hammer or other instrument (prior to attaching container 38) to force shaft 10 into the ground. Hollow tube 21 is positioned within well 34 below striking surface 42. Well 34 is sufficiently narrow relative to the driving instrument such that when block 28 receives the driving force, tube 21 is in a protected location beneath striking surface 42.

Figure 3:
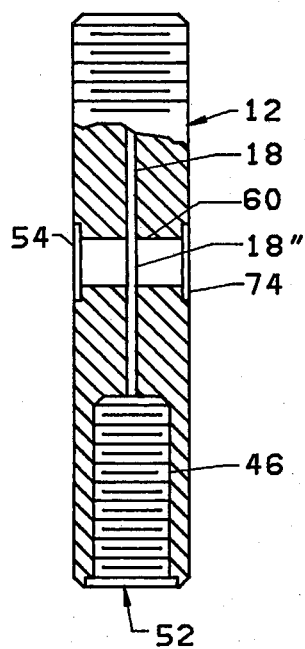
FIG. 3 is a partial sectional view of the upper sleeve illustrating the stop cock receptacle and shaft threaded connector receptacle.
Figure 6:
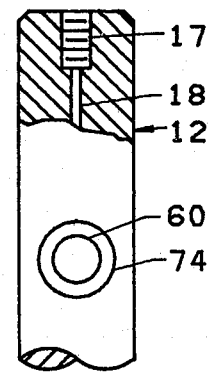
FIG. 6 is a partial sectional view of the upper sleeve illustrating the stop cock shaft receptacle and hollow tube connector receptacle.
Figure 4:
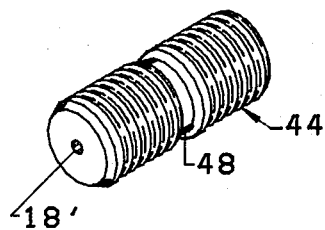
FIG. 4 is a perspective view illustrating the shaft threaded connector.

Shaft 10 may comprise a single integral structure or a structure separable into two or more parts for cleaning and storage. As depicted in FIGS. 1, 3 and 4, shaft 10 consists of three parts joined by threaded male connectors generally illustrated as 44 which mate with threaded female slots 46 of upper sleeves 12, body 14, and tip 16. Connectors 44 have circumferential recessions 48 for the receipt of O-rings 50 which when placed within O-ring slots 52 are compressed at the mating surfaces of the three shaft parts to maintain the gas tight integrity within bore 18. Connector capillary bores 18' longitudinally traverse connectors 44 to align with shaft bore 18 when connectors 44 are mated within slots 46, thereby forming a gas tight fitting between connector bore 18' and shaft bore 18.

Figure 5:
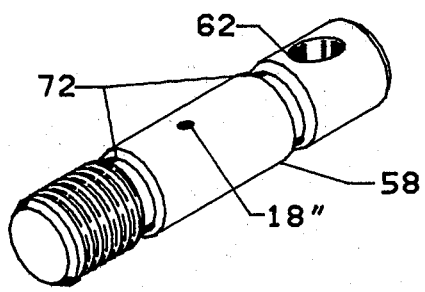
FIG. 5 is a perspective view illustrating the stop cock shaft.

Positioned between hollow tube 21 and tip 16 is a means (FIGS. 1 and 3), generally illustrated as 56, for regulating the flow of gases through tube 21 into and out of bore 18. Regulating means 56 comprises a stop cock having a shaft 58 mated within shaft receptacle 60 to allow rotational movement of shaft 58 about its longitudinal axis. Shaft 58 includes mounting hole 62 (FIG. 5) at one end for the receipt of a turnkey 64. Shaft 58 is held in place by washers 66, lock washer 68, and nut 70; O-rings 67 are mounted on shaft circumferential recessions 72 to fit within O-ring slots 74 to maintain a gas tight environment within bore 18. Stock cock opening 18" extends through shaft 58 along its lateral axis to permit rotation of shaft 58 and opening 18" therewith between an open position in which opening 18" is generally aligned with and in communication with shaft bore 18 as depicted in FIG. 1, and a closed position in which shaft 58 covers the opening of bore 18 resulting in a gas tight seal of bore 18. Rotational movement of shaft 58 is caused by rotation of turnkey 56; movement of gases in and out of bore 18 via tube 21 is permitted when stop cock shaft 58 is rotated to the open position.

The presence of regulating means 56 is a novel feature of this invention. All prior art lack any means for sealing the inside of shaft 10 from the outside atmosphere when vacuum container 38 is removed from the apparatus. Due to the small amount of soil gas collected in container 38, any non-soil gases present in the probe when the sample gases are withdrawn all contaminate the sample. Therefore, prior art apparatuses will deliver erroneous soil sample results because they cannot be purged of contaminant gases prior to collection of the testing sample.

Pre-purging requires the placement of the soil gas probe into the earth's soil at a sufficient depth such that openings 24 are in contact with the gas to be collected, and such that openings 24 are completely covered by the earth's soil to prevent atmospheric gases from entering the probe. A collecting container 38 is inserted into well 34 allowing tube 21 to puncture septum 40. Turnkey 64 is rotated to the open position allowing any remaining contaminant gases and some soil gas to be withdrawn through the probe into container 38. Contaminant gases may include atmospheric gases or other gases which may enter the probe to give an erroneous soil gas indication. Turnkey 64 is then rotated to the closed position to seal bore 18 and container 38 is removed, thereby completing the critical pre-purge steps. A second container for collecting the test sample 38 is then inserted onto tube 21. After a period of two to five minutes to allow the soil gases around tip 16 to reach equilibrium, turnkey 64 is rotated to the open position and a sample consisting entirely of soil gas is withdrawn into container 38. The turnkey 64 is then placed in the closed position and the probe is removed from the ground and taken to the lab for analysis of the collected sample.

In a preferred embodiment, regulating means 56 is positioned adjacent to or as close to tube 21 as possible to reduce the amount of contaminant gas which enters bore 18 when the purging collecting container 38 is replaced by the sample collecting container 38.

While the present invention has been described herein with reference to particular embodiments thereof, a latitude of modifications, various changes and substitutions are intended in the foregoing disclosure, and in some instances some features of the invention will be employed without a corresponding use of other features without departing from the scope of the invention as set forth.

I claim:

1. An apparatus for collecting sample gases from the earth's soil comprising a shaft means having a first end and a second end and a capillary bore means longitudinally traversing said shaft means, said second end of said shaft being implanted within the soil and having a structure defining a plurality of apertures in communication with said capillary bore means in order to transmit any gases from the earth's soil to said capillary bore means; a block means having a striking surface and attached rotatably to said first end of said shaft means such as to define a recess means with said first end of said shaft means terminating as the bottom of said recess means; a vacuum container means including a septum means and coupled removably within said recess means; means connected to said first end for puncturing said septum means and transmitting any soil gases from the capillary bore means into said vacuum container means behind said septum means; and means positioned in said shaft means for regulating the flow of soil gases through said capillary bore means.

2. The apparatus as recited in claim 1 wherein said shaft means additionally comprises a structure defining a generally diametrical bore means communicating with said capillary bore means such as to interrupt the longitudinal traverse of said capillary bore through the structure of the shaft means, said means for regulating comprises a regulating shaft means rotatably positioned through said diametrical bore means, said regulating shaft means having a regulating bore means extending diametrically through said regulating shaft means such as when the regulating shaft means is in a certain predetermined position, said regulating bore means communicates with both sections of the interrupted capillary bore in order to place both sections of the interrupted capillary bore in communication with each other through the regulating bore means and to enable soil gas to flow from one capillary bore section though the regulating bore means and into the other capillary bore section without disruption.

3. The apparatus of claim 2 wherein said first end of said shaft means additionally includes a structure defining a female receptacle means wherein said capillary bore means terminates, said means for puncturing said septum means and transmitting any soil gases comprises a male connector means threadably mating into said female receptacle means, a protruding hollow tube means having one end integrally bound within said male connector means such that said hollow tube means forms a gas tight fit with said capillary bore means when said male connector means is threadably mated into said female receptacle means.

4. The apparatus of claim 3 wherein said shaft means comprises a tip means, a lower body means threadably connected to said tip means, and an upper body means threadably attached to said lower body means.

5. The apparatus of claim 4 wherein said tip means has a structure defining a void space, and said plurality of apertures of said second end also defined within the structure of said tip means, said plurality of apertures of said tip means are in communication with said void space means which in turn is in communication with said capillary bore means in order to transmit any soil gases from the earth's soil to said capillary bore means.

6. The apparatus of claim 5 wherein said capillary bore means longitudinally traverses said upper body means and said lower body means and terminates at the juncture of said lower body means and said tip means.

7. The apparatus of claim 6 wherein said means for regulating and said means for puncturing said septum means and transmitting any soil gases as in said upper body means.

8. A process for collecting sample gases from the earth's soil comprising the steps of:
 (a) inserting into the earth's soil a soil gas probe means having a recess means in the upper most part thereof;
 (b) coupling into said recess means a first collecting container means having a first septum means that is punctured generally simultaneously with said coupling;
 (c) opening a regulating means to allow any contaminant gases to be withdrawn from the probe means into the first collecting container means while simultaneously allowing gases from the soil to be withdrawn into the probe means;
 (d) closing the regulating means;
 (e) uncoupling the first collecting container means from said recess means;
 (f) coupling into said recess a second collecting container means having a second septum means that is punctured generally simultaneously with said coupling; and
 (g) opening the regulating means to allow the soil gases from the probe means to be withdrawn into the second collecting container means.

9. The process of claim 8 additionally comprising uncoupling said second collecting container means from said recess means.

10. The process of claim 9 additionally comprising removing said soil gas probe means from the earth's soil.

* * * * *